United States Patent [19]
Krygier et al.

[11] Patent Number: 4,889,491
[45] Date of Patent: Dec. 26, 1989

[54] DENTAL THROAT SHIELD

[76] Inventors: S. James Krygier, P.O. Box 155, Montchanin, Del. 19710; Alexander DeMayo, 10 Ferndale Dr., Runnemede, N.J. 08078

[21] Appl. No.: 196,533

[22] Filed: May 20, 1988

Related U.S. Application Data

[63] Continuation-in-part of Ser. No. 167,543, Mar. 14, 1988, abandoned.

[51] Int. Cl.⁴ ............................................... A61C 5/14
[52] U.S. Cl. .................................................... 433/136
[58] Field of Search ...................... 433/136, 140, 137; 128/12

[56] References Cited

U.S. PATENT DOCUMENTS

| | | | |
|---|---|---|---|
| 2,937,445 | 5/1960 | Erickson | 433/93 |
| 3,916,880 | 11/1975 | Schroer | 128/12 |
| 4,511,329 | 6/1985 | Diamond | 433/140 |

*Primary Examiner*—Robert Peshock
*Attorney, Agent, or Firm*—Connolly & Hutz

[57] ABSTRACT

A dental throat shield includes a U-shaped support member having a pair of legs interconnected by a bight portion. A shield member is bowed or arcuate and made of a shape retaining yet flexible material so as to conform to and cover the throat area. A plurality of openings are provided in the shield member to permit the patient to breathe.

14 Claims, 1 Drawing Sheet

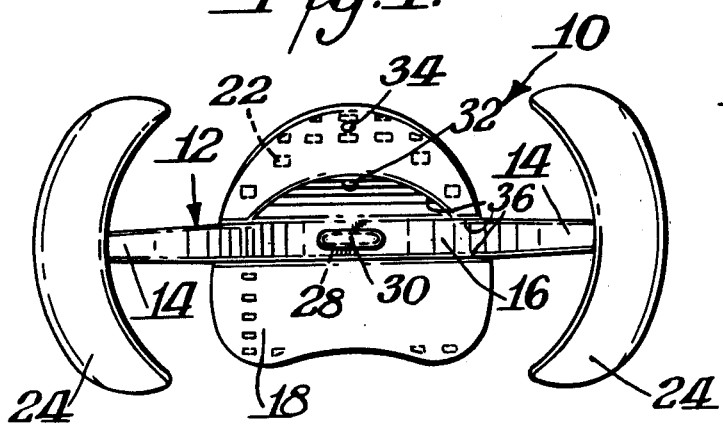
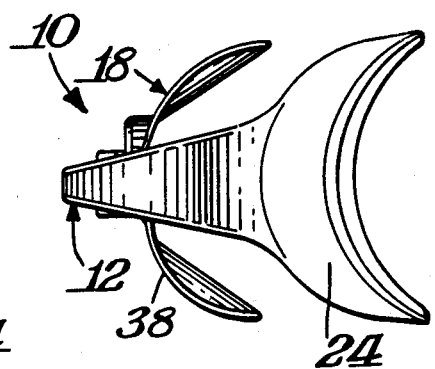
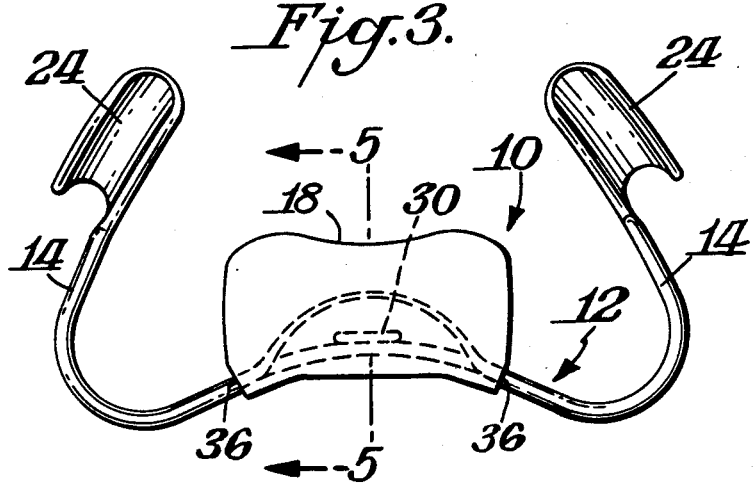
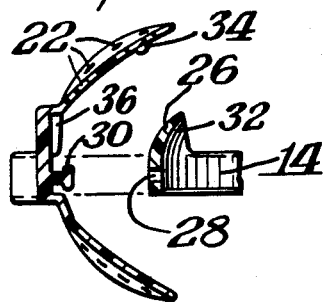
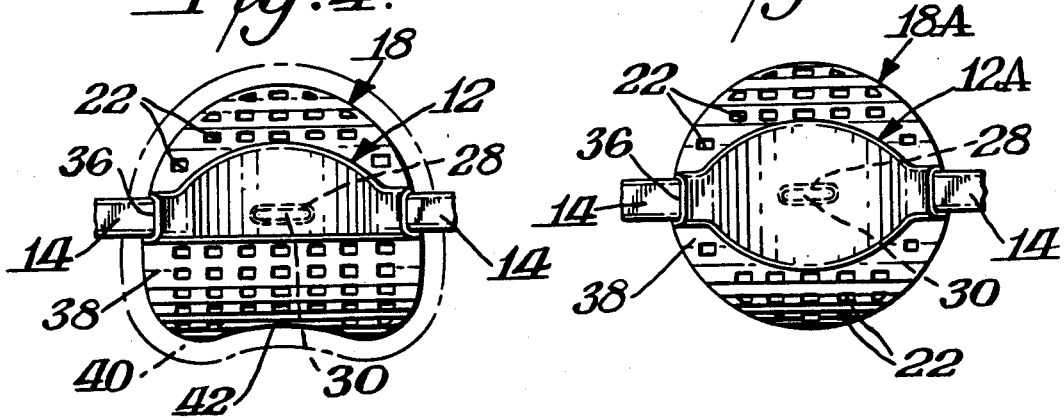
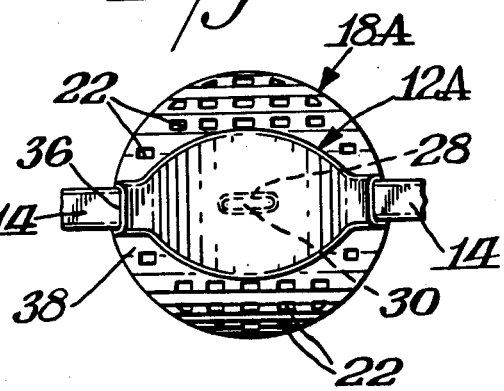

DENTAL THROAT SHIELD

CROSS REFERENCE TO RELATED APPLICATION

This application is a continuation in part of Serial No. 167,543, filed Mar. 14, 1988 and now abandoned.

BACKGROUND OF THE INVENTION

Various devices exist for assisting a dentist or othodontist in treating a patient to assure that the patient's mouth remains open. For example, U.S. Pat. Nos. 3,241,550, 3,916,880 and 4,200,089 describe mouth or cheek retractors. The device of U.S. Pat. No. 3,916,880 additionally includes a member for displacing the patient's tongue. U.S. Pat. Nos. 735,762, 1,157,565, 2,476,675 and 4,179,815 exemplify various dental props for holding open the patient's mouth. Such devices also include ancillary members which serve various functions such as mirrors and tongue shields.

A serious drawback with such prior art approaches is that they do not shield the patient's throat. Consequently, if the patient's head is completely bent back, there is a danger that objects can fall into and down the throat, esophagus or trachea. Alternatively, if the patient's head must be maintained in its normal generally vertical orientation, the dentist is restricted in the degree of freedom in the dental treatment.

There is, therefore, a need for a dental device which takes advantage of various prior art approaches while additionally shielding the throat, esophagus and trachea.

SUMMARY OF THE INVENTION

An object of this invention is to provide a device which would effectively shield the patient's throat.

A further object of this invention is to provide such a device which could additionally function as a cheek retractor.

In accordance with this invention, a support member is provided for insertion in the mouth. A shield is attached, either integrally or detachably, to the support member. The shield is bowed or arcuate in its normal condition and is made of a shape retaining and flexible material so as to conform to and cover the throat area. A plurality of holes are formed in the shield to permit the patient to breathe.

In a preferred form of this invention, the support member is U-shaped with a pair of legs interconnected by a bight portion. The shield is attached to the bight portion. The support member is made of a resilient or springy material, and its free ends are formed as troughs whereby the support member additionally functions as a cheek retractor.

THE DRAWINGS

FIG. 1 is a front elevation view of a dental throat shield in accordance with this invention;

FIG. 2 is a side elevation view of the shield of FIG. 1;

FIG. 3 is a bottom plan view of the shield shown in FIGS. 1-2;

FIG. 4 is a rear elevation view of a modified shield;

FIG. 5 is a cross-sectional exploded view taken through FIG. 3 along the lines 5—5; and FIG. 6 is a view similar to FIG. 5 showing a modified shield.

DETAILED DESCRIPTION

The drawings illustrate a dental shield device 10 which includes a laterally bowed U-shaped support member 12 having a pair of legs 14, 14 interconnected by a bight portion 16. Shield member 18 in its normal condition is of vertically bowed or arcuate shape and is made of a shape retaining yet flexible material so that it will conform to and cover the throat area of the patient when device 10 is inserted in the mouth. Shield member 18 is provided with a plurality of holes 22 throughout its area. For the sake of clarity, not all of the holes 22 have been illustrated. Shield member 18 thus takes the form of a resilient screen or perforated web spanning the patient's mouth. The size, shape and number of the holes 22 are not critical as long as the open areas through shield member 18 are large enough to permit the patient to easily breathe, yet not so large as to allow objects to fall down the patient's throat, esophagus or trachea.

Shield device 10 is preferably made of known plastic materials used in the dental art. Member 18, however, would not be made as hard and stiff as the remainder of device 10.

In the preferred form of this invention, support member 12 also functions as a cheek retractor by including a trough 24, 24 at the free end of each leg 14, 14. Troughs 24, 24 may be conveniently formed by bending flange elements provided at each free end as best shown in FIG. 3. Alternatively, troughs 24, 24 may be separate elements connected to legs 14, 14. In use, the outer sides of troughs 24, 24 would be outside the mouth with the lips of the patient in the troughs and with the remainder of device 10 within the mouth. Support member 12 is made of a springy material to enhance its cheek retracting ability. Troughs 24, 24, however, need not be particularly resilient.

Although support member 12 has been described as a cheek retractor, it may take other forms, such as a simple mouth prop, as long as it functions to locate shield member 18 over the throat area.

The invention may be practiced with shield member 18 integral with its support member by device 10 being molded in one-piece construction. The preferred practice of the invention, however, is to detachably mount shield member 18 to support member 12. As a result, the same support member may be used for different shield members. FIGS. 1 and 5 illustrate a manner of detachable mounting. As shown therein, bight section 16 is provided with an upwardly extending flange 26 which is shaped to conform to the shape of shield member 18 so that after assembly, flange 26 and shield member 18 fit snugly against each other. An aperture 28 is provided completely through bight section 16. Shield member 18 includes a T-shaped post 30 for snapping through aperture 28 with its free end being on the remote side of bight section 16 (FIG. 3). Because of the resilient materials and rounded edges of post 30, shield member 18 may also be detached by pressing shield member 18 away from bight section 16.

A nub 32 is located on flange 26 and a nub 34 is located on shield member 18. These nubs serve as orientation indicators which could be important where the upper and lower portions of shield member 18 are of similar but not identical shape. Thus, the user would know that shield member 18 is properly oriented with both nubs 32, 34 are on the same side of bight section 16.

Advantageously, shield member 18 is mounted against the rear surface of bight section 16. Thus, if the patient's tongue presses against shield member 18, the force is to maintain shield member 18 in contact with support member 12, rather than to dislodge shield member 18.

The side sections of shield member 18 are formed as channels 36, 36 which fit over support member 12 so as to position shield member 18 into intimate contact with the throat area despite the fact that its location of mounting bight section 16 is between shield member 12 and the throat.

Shield member 18 may be made in various sizes to better fit different patients. Alternatively, the number of sizes could be minimized by providing peripheral extensions joined by score lines to its inner areas to permit the size to be varied. FIG. 4, for example, illustrates shield member 18 to include a central area 38 (shown in solid) with a peripheral extension 4 (shown in phantom) joined thereto at score line 42. Further extensions may be provided beyond extension 40. If it is found that the shield member with extension 40 is too large and that the proper size would simply be central area 38, extension 40 could be readily removed by tearing at score line 42.

FIG. 6 illustrates a variation wherein shield member 18A is symmetrically shaped with identical upper and lower portions. Similarly support member 12A would also be symmetrically shaped.

Shield device 10 thus provides an effective shield for a patient's throat, esophagus and trachea without impairing the patient's ability to breathe. Additionally, by mounting shield member 18 on a support, such as support member 12, device 10 has the added advantage of functioning as a cheek retractor.

What is claimed is:

1. A dental throat shield comprising a support member, a shield member attached to said support member, said support member being laterally bowed and made of a springy material, said shield member being vertically bowed shaped, said bowed shaped shield member being made of a resilient and shape retaining and soft and flexible material so as to conform to and cover the throat area of a patient, and a plurality of openings throughout the area of said shield member with said openings being of a size to permit the patient to breathe and to prevent objects from falling into the patient's posterior throat area, esophagus and trachea.

2. The shield of claim 1 wherein said support member is U-shaped with a pair of legs interconnected by a bight portion, and said shield member being mounted to said bight portion.

3. The shield of claim 2 including a through at each of said free ends, and said support member being made of a springy material to comprise a cheek retractor.

4. The shield of claim 3 wherein said shield member is detachably mounted to said support member.

5. A dental throat shield comprising a support member, a shield member attached to said support member, said shield member being bowed shaped, said shield member being made of a shape retaining and flexible material so as to conform to and cover the throat area of a patient, a plurality of openings in said shield member to permit the patient to breathe and to prevent objects from falling into the patient's posterior throat area, esophagus and trachea, said support member being U-shaped with a pair of legs interconnected by a bight portion, said shield member being mounted to said bight portion, a through at each of said free ends, said support member being made of a springy material to comprise a cheek retractor, said shield member being detachably mounted to said support member, a hole in said bight portin, and a T-shaped post on said shield member for detachable insertion through said hole.

6. The shield of claim 5 wherein said support member has a front surface and a rear surface, said rear surface being adapted to be disposed toward the patient's throat, and said shield member being disposed against said rear surface whereby a force from the patient's tongue urges said shield member against said support member.

7. The shield of claim 6 wherein said shield member is channel shaped where said shield member contacts said bight section to dispose the main portion of said shield member rearwardly of said rear surface.

8. The shield of claim 7 including an arcuate flange connected to said bight section snugly fitting against said shield member.

9. The shield of claim 8 including indicating means on said shield member for properly orienting said shield member on said support member.

10. The shield of claim 9 wherein said shield member includes a central section, and a peripheral extension connected to said central section by a score line.

11. A dental throat shield comprising a support member, a shield member attached to said support member, said shield member being bowed shaped, said shield member being made of a shape retaining and flexible material so as to conform to and cover the throat area of a patient, a plurality of openings in said shield member to permit the patient to breathe and to prevent objects from falling into the patient's posterior throat area, esophagus and trachea, said support member being U-shaped with a pair of legs interconnected by a bight portion, said shield member being mounted to said bight portion, a through at each of said free ends, said support member being made of a springy material to comprise a cheek retractor, said shield member including a central section, and a peripheral extension connected to said central section by a score line.

12. A dental throat shield comprising a support member, a shield member attached to said support member, said shield member being bowed shaped, said shield member being made of a shape retaining and flexible material so as to conform to and cover the throat area of a patient, a plurality of openings in said shield member to permit the patient to breathe and to prevent objects from falling into the patient's posterior throat area, esophagus and trachea, said shield member including a central section, and a peripheral extension connected to said central section by a score line.

13. The shield of claim 3 wherein said shield member is integral with said support member.

14. The shield of claim 1 wherein said shield member is integral with said support member.

* * * * *